US 7,887,591 B2

United States Patent
Aebi et al.

(10) Patent No.: US 7,887,591 B2
(45) Date of Patent: Feb. 15, 2011

(54) INTERVERTEBRAL IMPLANT COMPRISING JOINT PARTS THAT ARE MOUNTED TO FORM A UNIVERSAL JOINT

(75) Inventors: Max Aebi, Bern (CH); Dominique Burkard, Gretzenbach (CH); Robert Frigg, Bettlach (CH); Beat Lechmann, Bettlach (CH); Robert Mathys, Jr., Bettlach (CH); Paul Pavlov, Nijmegen (NL)

(73) Assignee: Synthes USA, LLC, West Chester, PA (US)

( * ) Notice: Subject to any disclaimer, the term of this patent is extended or adjusted under 35 U.S.C. 154(b) by 663 days.

(21) Appl. No.: 10/538,542

(22) PCT Filed: Dec. 17, 2002

(86) PCT No.: PCT/CH02/00706

§ 371 (c)(1),
(2), (4) Date: Jun. 8, 2007

(87) PCT Pub. No.: WO2004/054477

PCT Pub. Date: Jul. 1, 2004

(65) Prior Publication Data

US 2008/0119933 A1    May 22, 2008

(51) Int. Cl.
*A61F 2/44*    (2006.01)
(52) U.S. Cl. .................................. 623/17.15; 623/17.11
(58) Field of Classification Search ... 623/17.11–17.16; 403/72–74
See application file for complete search history.

(56) References Cited

U.S. PATENT DOCUMENTS

| | | | |
|---|---|---|---|
| 4,759,769 A | | 7/1988 | Hedman et al. |
| 5,333,347 A | * | 8/1994 | Stranders ................... 15/220.1 |
| 5,762,410 A | * | 6/1998 | Lutz ............................ 312/111 |
| 6,533,791 B1 | | 3/2003 | Betz et al. |
| 2002/0052656 A1 | * | 5/2002 | Michelson ................ 623/17.11 |
| 2003/0208273 A1 | * | 11/2003 | Eisermann et al. ........ 623/17.14 |
| 2003/0233145 A1 | * | 12/2003 | Landry et al. ............. 623/17.11 |
| 2004/0106998 A1 | * | 6/2004 | Ferree ...................... 623/17.16 |

FOREIGN PATENT DOCUMENTS

CA    2332822    11/1999

* cited by examiner

*Primary Examiner*—Thomas C. Barrett
*Assistant Examiner*—Michael T Schaper
(74) *Attorney, Agent, or Firm*—Stroock & Stroock & Lavan, LLP

(57) ABSTRACT

An intervertebral implant (1), specifically an artificial intervertebral disk, with a central axis (2), an upper section (10), suitable for laying onto the base plate of a vertebral body lying on top and a lower section (20), suitable for laying onto the cover plate of a vertebral body lying below, wherein
  A) the upper section (10) is provided with a ventral side area (11), a dorsal side area (12), two lateral side areas (13,14), a top apposition surface (15) and a bottom surface (16);
  B) the lower section (20) is provided with a ventral side area (21), a dorsal side area (22), two lateral side areas (23,24), a bottom apposition surface (25) and a top surface (26);
  C) the two sections (10,20) are moveable in relation to each other by means of one joint (30) arranged between the two sections (10;20), wherein
  D) the joint (30) is a universal joint with two swivel axles (3;4) standing perpendicular to each other.

7 Claims, 4 Drawing Sheets

INTERVERTEBRAL IMPLANT COMPRISING JOINT PARTS THAT ARE MOUNTED TO FORM A UNIVERSAL JOINT

BACKGROUND OF THE INVENTION

The invention relates to an intervertebral implant and to a process for the replacement of a defect, natural intervertebral disk by an intervertebral implant.

After removal of a damaged, natural intervertebral disk or a damaged nucleus pulposus of an intervertebral disk, implants or prostheses are inserted into the intervertebral space of two neighbouring vertebral bodies. This suggests the idea of restoring the situation as much as possible to a natural state, i.e. specifically to restore the original height of the intervertebral disk and thus the original distance between the two neighbouring vertebral bodies. Furthermore, the patient should be able to carry out movements of the neighbouring vertebral bodies relative to each other in the natural way, thereby incurring as little obstruction as possible. This essential feature of this system is its ability to retain the freedom of movement in forward/reverse inclination, i.e. flexion and extension of the vertebral bodies, and in lateral bending of the vertebral bodies within the natural limits. The natural sinews and muscles along the spinal column are in general left intact so that they further stabilise the movements of a mechanical intervertebral disk prosthesis.

A characteristic intervertebral disk endoprosthesis is state of the art from DE-A 35 29 761 BÜTTNER. This known intervertebral disk endoprosthesis basically consists of two symmetric closing plates with concave sliding surfaces facing each other, and each having an external surface for laying on the base plate, or the cover plate of the adjoining vertebral body, and a distance piece positioned between the closing plates with convex sliding surfaces arranged complementary to the concave sliding surfaces on the closing plates. The sliding surfaces are designed in one embodiment as section surfaces of a cylinder coat area, wherein the sliding surfaces arranged on the two closing plates are provided complementary to each of the adjoining sliding surfaces at the distance piece, and two complementary sliding surfaces form the articulation surfaces, which can be moved towards each other, of a joint element rotating around a swivel axle. The joint comprises an upper and a lower joint element, each of which has one swivel axle. The two swivel axles are set at 90° to each other. The disadvantages of this known intervertebral disk endoprosthesis is that a) the arrangement of an intervertebral disk endoprosthesis with only one fulcrum does not take sufficient account of the overlaying swivel movements transferred by the natural intervertebral disk, specifically in the case of anterior-posterior and in lateral flexion, which in the natural intervertebral disk are independent of each other;

b) the vertebral joint is put under strain by swivel movements, specifically with translation in the anterior-posterior direction (face joint), which could cause pain for the patient;

c) disadvantageous friction forces are generated by two articulating surfaces sliding on each other. This also leads to wear on the surfaces, including also abrasion and resistance in movement of the joint elements. There is also the risk of the "stick slip" effect;

d) a mechanical intervertebral disk prosthesis can scarcely prevent the further degeneration of the affected movement segments. Restoration of the original freedom of movement significantly reduces pain, with the resulting improvement to the patient's quality of life. A review of treatment will, however, have to be undertaken if pain recommences. This will normally involve complete removal of an intervertebral disk prosthesis of the standard model and a stiffening of the movement segment. This operation represents extreme discomfort and strain on the patient; and e) the form of contact areas to the neighbouring vertebral bodies is generally not taken into account. The conventional types of intervertebral disk prosthesis implants have flat contact areas, which are often supplemented with keel-type elevations.

BRIEF SUMMARY OF THE INVENTION

The invention is intended to remedy this situation. The invention is based on the task of creating an intervertebral implant that is provided with joints having with minimum friction surfaces.

The invention solves the task with an intervertebral implant and with a process for replacing a defect, natural intervertebral disk by an intervertebral implant.

The advantages achieved by the invention can generally be seen in that with the intervertebral implant according to the invention
  the swivel movements in anterior-posterior and lateral direction are independent of each other;
  no translation movements of the vertebral bodies adjoining the implant are permitted, which relieves strain on the face joints; and
  the friction surfaces of the moved elements are restricted to small cylindrical or polygon-shaped rotation bodies and are thus kept at a minimum.

In a preferred embodiment of the intervertebral implant according to the invention, the two joints comprise three joint sections, wherein the central joint section is arranged as a frame and this frame is connected on the one hand to the lower joint section by means of two axles arranged coaxial to the first swivel axle in a way that allows rotation around the first swivel axle, and on the other hand connected to the upper joint section by means of a further axle arranged coaxial to the second swivel axle in a way that allows rotation around the second swivel axle. The swivel axles can thereby be arranged in a warped manner or in a plane or intersecting.

In a further embodiment of the intervertebral implant according to the invention, the central joint section is arranged as a cross.

In a further embodiment of the intervertebral implant according to the invention the central joint section is arranged as an angle. This means that only one axle coaxial to the relevant swivel axle is necessary for each joint, by means of which the advantage is achieved that the two joints are realised by fewer components.

In a further embodiment of the intervertebral implant according to the invention, a means can be attached to the two sections from the ventral side areas which holds the two sections ventral at a fixed distance relative to each other. This measure provides the advantage that the two sections for insertion into the intervertebral space can be brought to a position with fixed height and can be moved around the joint after insertion into the intervertebral space and can be placed on the base or cover plate of the adjoining vertebral body.

In a further embodiment of the intervertebral implant according to the invention, the means allows temporary blocking of the mobility of the two sections around the joint. This measure provides the advantage that the joint integrated in the intervertebral space can be blocked by a minimum invasive operation. This is particularly advantageous in cases where the patient suffers from post-operative pain, i.e. where degeneration of the affected spinal column segment continues and the surgeon is considering a fusion of the affected vertebra. The means can preferably be attached to the two ventral side areas of the two sections. With this subsequent, secondary blocking of the mobility of the two sections around the joint, the intervertebral implant is stiffened and transferred to an arthrodesis implant (fusion cage).

In a further embodiment of the intervertebral implant according to the invention, the means for blocking the joint comprises two insert pieces. The two insert pieces can be fixed by means of screws on the lower joint sections parallel to the second swivel axle. If the insert pieces are being used, the upper section and the lower section will lean against each other so that there can be no swivel movement of one of the sections in relation to the other around the two swivel axles.

In a further embodiment of the intervertebral implant according to the invention, the means comprises an insert, which can be placed into each depression on the surfaces of the upper and lower section opposite each other. These depressions are preferably provided as dovetail guides that are open on the ventral side areas, so that the ends of the insert arranged complementary to the dovetail guides can be inserted from ventral into the dovetail guides. This provides the advantage that the mobility of the two sections around the joint is blocked due to the positioning of the insert. The rigidity of the blocking can be increased when the dovetail guides are designed so that they are reduced is size towards the central axis of the intervertebral implant, which creates additional wedging of the insert in the dovetail guides.

In a further embodiment of the intervertebral implant according to the invention, the means comprise two parallel inserts that can be slid parallel to the lateral side surfaces between the two sections and come to rest on the surfaces of the two sections that face each other. Both inserts can be fixed at the lower section of each by means of a screw.

In a further embodiment of the intervertebral implant according to the invention, the two sections are provided with drill holes for receiving the bone fixation means, specifically bone screws, wherein the drill holes are provided with longitudinal axes that stand perpendicular to the central axis. Preferably two drill holes will pass through one of the two sections from the ventral side area to the apposition surface. The longitudinal axes, if only an axial fixing of the intervertebral implant is provided, will then be able to stand only perpendicular to the central axis from a lateral perspective, or, if fixing of the intervertebral implant with stable angle is provided, will also from a lateral perspective diverge from the inner surfaces of the two sections against the apposition surfaces.

In a further embodiment of the intervertebral implant according to the invention, the drill holes for receiving the bone fixation means are provided with internal threads, which allows additional, rigid fixing of the bone fixation means in the two sections. The drill holes preferably have a conical shape so that a stronger fixing of the bone fixation means to each of the two sections can be achieved by the resulting conical thread connections between the internal threads and the external threads on the heads of the bone fixation means.

The process according to the invention is intended primarily for replacing a defect, natural intervertebral disk by an intervertebral implant and comprises the following steps:

A) blocking of the joint(s) of an intervertebral implant by means of a special device placed in a certain position of the joint(s);

B) insertion of the intervertebral implant into the intervertebral space to be treated;

C) release and removal of the device inserted into the intervertebral implant for blocking the joint(s). Blocking the joint provides the advantage that the moveable sections with the external apposition surfaces can be inserted more easily into the intervertebral space to be treated.

In a further application of the process according to the invention, this comprises the subsequent blocking of the joint (s) on the implanted intervertebral implant by means of the device intended for blocking the joint(s). This provides the advantage that if the patient should suffer from post-operative pains or in case of a further degeneration of the movement segment, the joint(s) on the intervertebral implant are blocked post-operative by the insertion of the means intended for this purpose. This subsequent blocking can be achieved with an minimally invasive, preferably a laprascopic operation. The intervertebral implant then assumes the function of a cage, so that the affected movement segment of the spinal column can be stiffened.

The invention and refinements of the invention are described in more detail below on the basis of a partially schematic illustration of one embodiment.

DETAILED DESCRIPTION OF THE INVENTION

Figure 1:
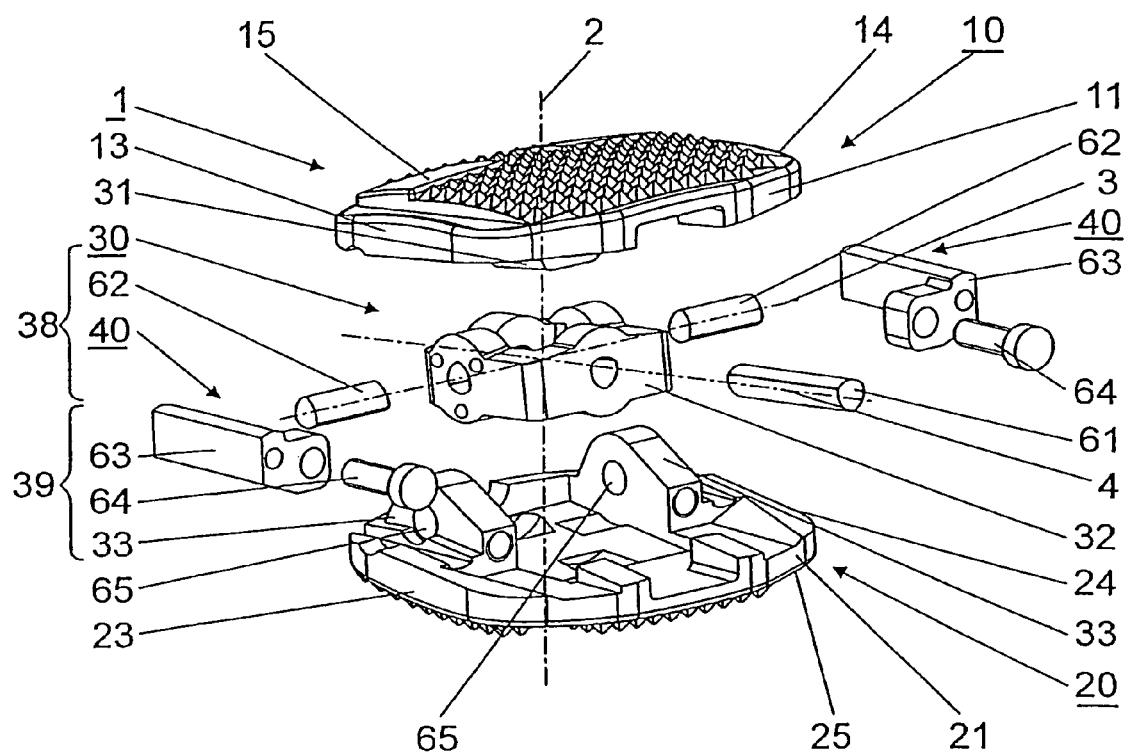
FIG. 1 shows an explosion diagram of one embodiment of the intervertebral implant according to the invention.

An embodiment of the intervertebral implant according to the invention 1 is illustrated in FIG. 1 and comprises an upper section 10 with an upper apposition surface 15 arranged perpendicular to the central axle 2 for laying onto the base plate of a neighbouring vertebral body, a lower section 20 with a lower apposition surface 25 arranged perpendicular to the central axle 2 for laying onto the cover plate of the neighbouring vertebral body and a joint 30. The upper section 10 and the lower section 20 are linked in a way that allows movement in relation to each other by means of the joint 30, wherein the mobility of the upper section 10 relative to the lower section 20 around a first swivel axle 3 arranged perpendicular to the central axle 2 is limited within an angle range of between +10° and −6° and around a second swivel axle 4 arranged perpendicular to the central axle 2 and vertical to the first swivel axle 3 is limited within an angle range of ±7°.

The joint 30 is arranged as a universal joint and comprises a central joint section 32 arranged as a frame, which central joint section 32 has a central joint section 32 with two axles 62 arranged coaxial to the first swivel axle 3, which in two complementary drill holes 65 on the lower joint sections 33 are carried in a way permitting rotation around the first swivel axle 3. A further axle 61 arranged coaxial to the second swivel axle 4 is attached to the central joint section 32 and placed in a complementary drill hole (not shown in the illustration) at the upper joint section 31 rotating around the second swivel axle 4. The axles 61;62 can be provided with a circular or polygon-type cross-section surface in the cross-section from a perspective orthogonal to the swivel axle 3;4. The joint 30 in the embodiment illustrated here is blocked by means 40, which comprises two insert pieces 63 that are fixed parallel to the second swivel axle 4 on the lower joint sections 33 by means of screws 64. If insert pieces 63 have been applied, the upper section 10 and the lower section 20 will be supported against each other so that neither a swivel movement of one of the sections 10;20 relative to the other around the first swivel axle 3, nor a swivel movement of one of the sections 10;20 relative to the other around the second swivel axle 4 will be possible.

The two sections 10;20 and the central joint section 32 are held together by the axles 61;62 fixed in the central joint section 32, which axles are carried in a way allowing rotation in the drill holes 65 in the lower joint section 33 and a drill hole (not illustrated) in the upper joint section 31 around the swivel axles 3;4

Figure 2:
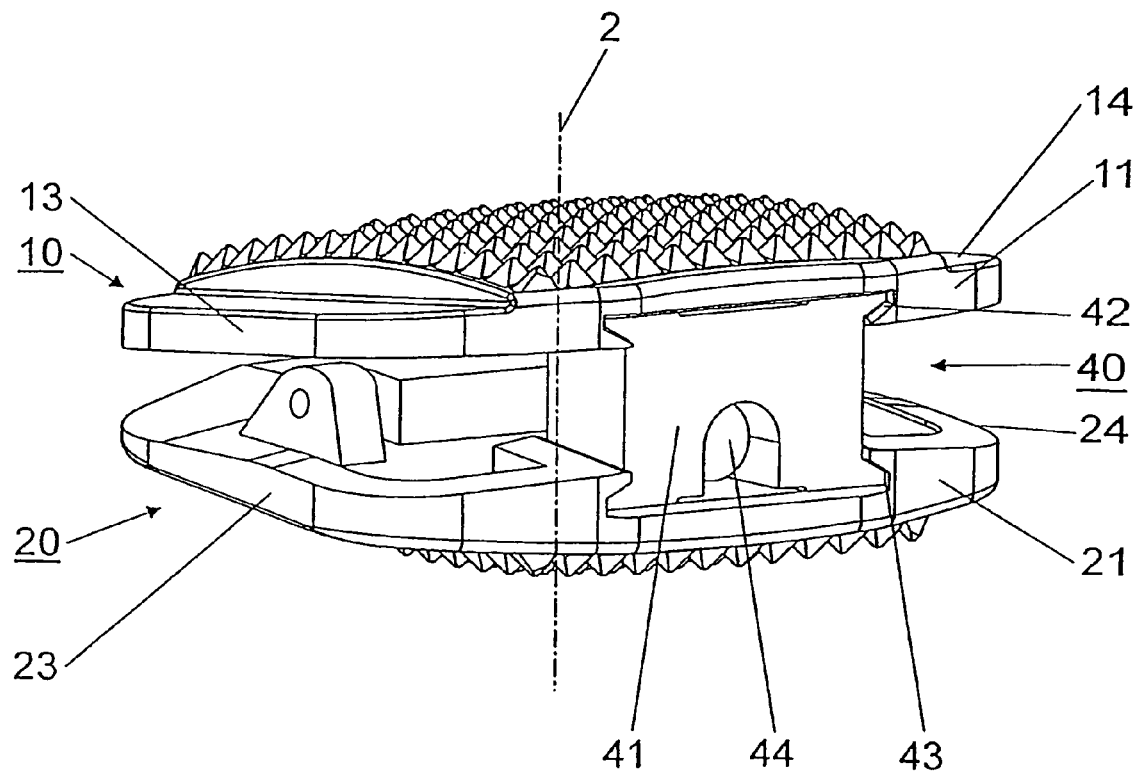
FIG. 2 shows a perspective view of the embodiment of the intervertebral implant according to the invention shown in FIG. 1 in assembled state.

The embodiment of the intervertebral implant according to the invention illustrated in FIG. 2 differs from the embodiment illustrated in FIG. 1 only in that the means 40 is designed differently. The means 40 comprises in the embodiment described here an insert 41 that can be slid in from the ventral side areas 11;21 of the two sections 10;20 perpendicular to the central axis 2 and parallel to the lateral side areas 13;14;23;24 of the two sections 10;20. The insert 41 is slid in two depressions 42;43, provided in the form of dovetail guides. The insert 41 is inserted from the ventral side areas 11;21 of the two sections 10;20 into the depressions 42;43 composed as dovetail guides and fitted to the lower section 20 by means of a screw 44. The insert 41 is furthermore arranged in the terminal state complementary to the depressions 42;43, so that the two sections 10;20 with fitted insert 41 are fixed relative to each other parallel to the central axis 2.

Figure 3:
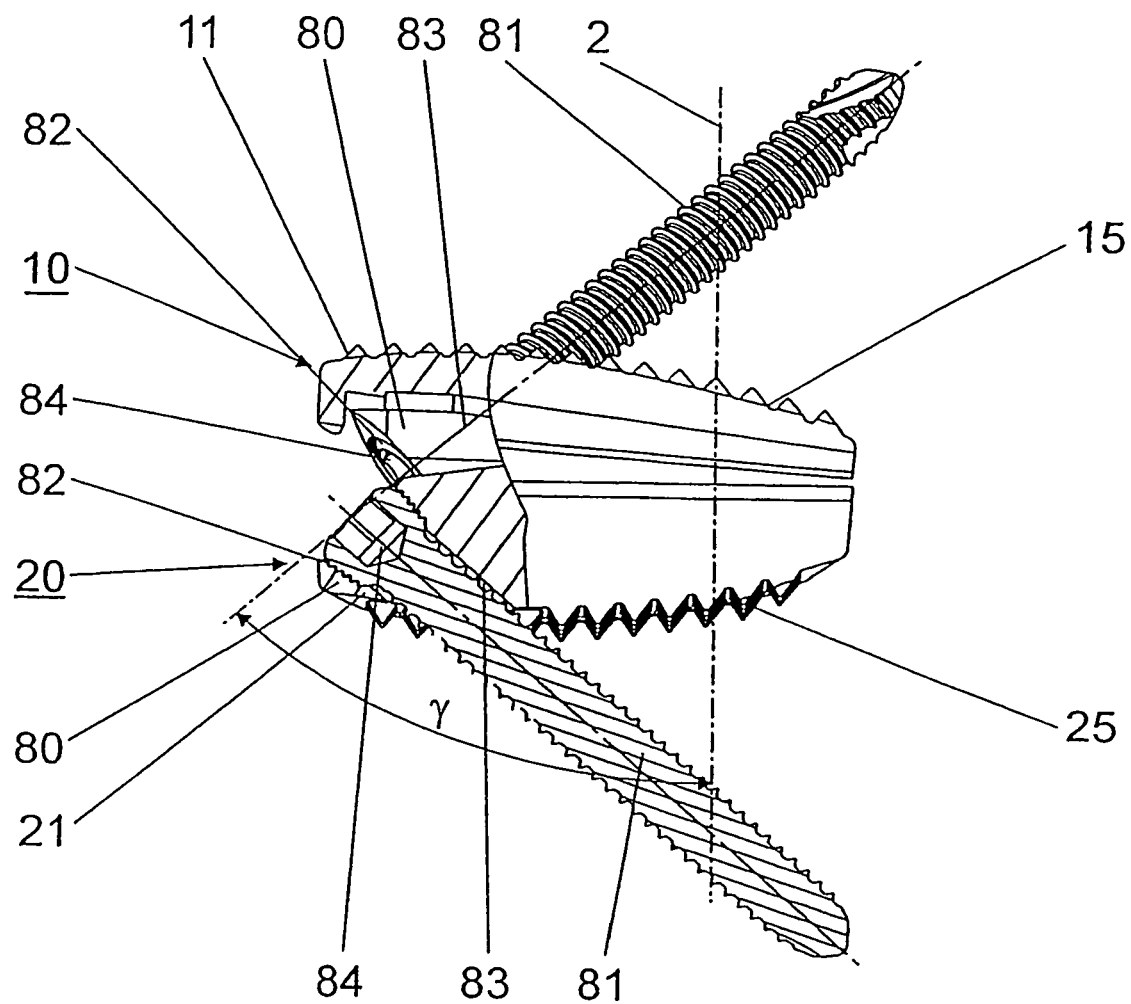
FIG. 3 shows a lateral view of a further embodiment of the intervertebral implant according to the invention.
Figure 4:
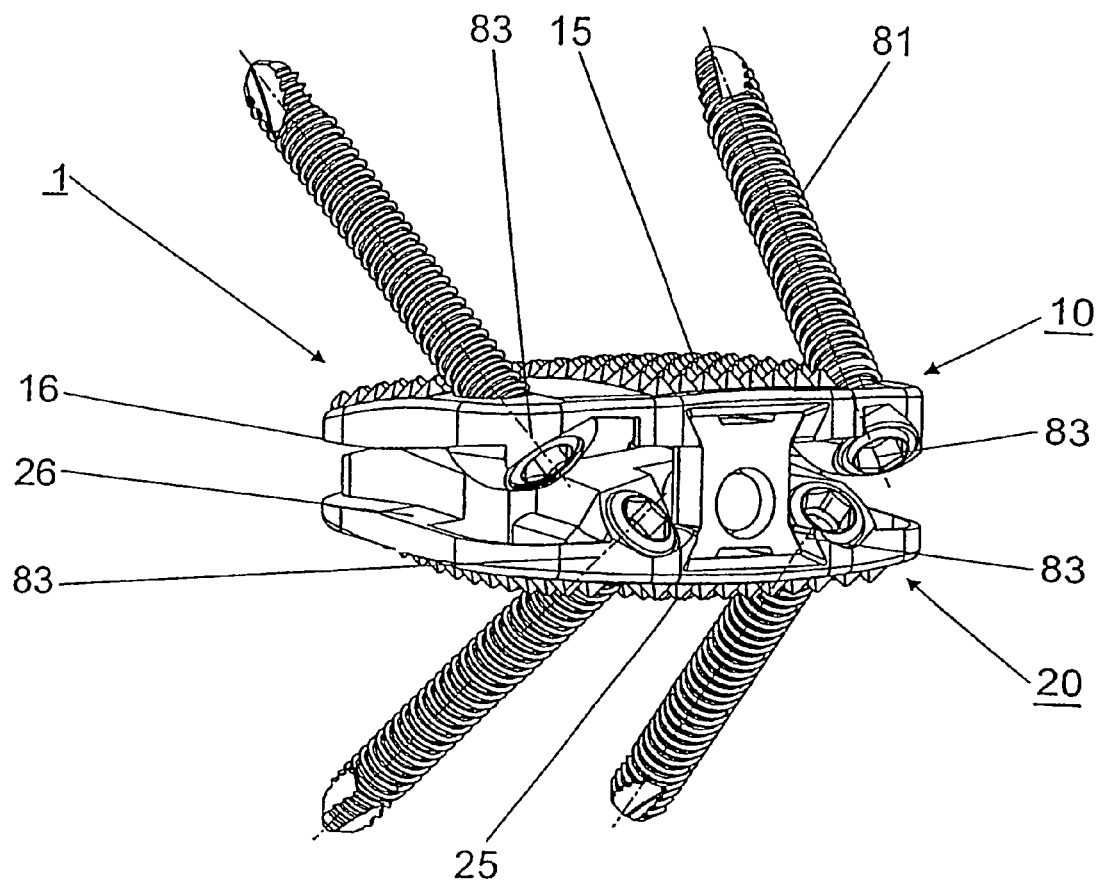
FIG. 4 shows a perspective view of the embodiment according to FIG. 3 from the ventral side.

FIG. 3 illustrates an embodiment of the intervertebral implant 1 according to the invention, which differs from the embodiment illustrated in FIG. 1 and FIG. 2 only in that the two sections 10;20 also comprise drill holes 80 for receiving the bone fixation means 81, whereby the bone fixation means 80 is provided in this case as bone screws. The drill holes 80 are provided with longitudinal axes 83 that form an angle γ with the central axis 2. In addition, each two drill holes 80 (FIG. 4) run trough one of the two sections 10;20 from the ventral side area 11;21 to the apposition surface 15;25. The longitudinal axes 83 of the drill holes 80 are standing perpendicular to the central axis 2 both from a lateral perspective (FIG. 3) and from a ventral perspective (FIG. 4). The drill holes 80 are furthermore provided in conical design and tapering towards the apposition surfaces 15;25 and provided with internal threads 82 that are used for screwing reception of the screw heads 84 of the bone fixation device 81 realised here in the form of bone screws and provided with complementary external threads.

The invention claimed is:

1. An intervertebral implant comprising a central axis, an upper section, suitable for laying onto a base plate of a vertebral body lying above, and a lower section suitable for laying onto a cover plate of a vertebral body lying below, wherein:

the upper section has a ventral side area, a dorsal side area, two lateral side areas, a top apposition surface, a bottom surface and a first projection extending from the bottom surface, the first projection including a first drill hole, the ventral side area including a first depression;

the lower section has a ventral side area, a dorsal side area, two lateral side areas, a bottom apposition surface, a top surface and second and third projections extending from the top surface, the second and third projections including second and third drill holes, respectively, the ventral side area including a second depression; and a frame shaped, central joint section located between the upper and lower sections so that the upper section is moveable with respect to the lower section, the central joint section including a central bore and first, second, third and fourth drill holes, the first projection extending from the bottom surface of the upper section being receivable within the central bore formed in the central joint section, the central joint section being receivable between the second and third projections extending from the top surface of the lower section so that a first axle is receivable in the first and second drill holes formed in the central joint section and the first drill hole formed in the first projection, a second axle is receivable in the third drill hole formed in the central joint section and the second drill hole formed in the second projection and a third axle is receivable in the fourth drill hole formed in the central joint section and the third drill hole formed in the third projection; and a removable insert for temporary blocking movement of the upper and lower sections such that the insert maintains the upper and lower sections, measured at their ventral side areas, at a fixed distance from each other, the insert including a lower end and an upper end, the upper end being receivable in the first depression, the lower end being receivable in the second depression, the first and second depressions being dovetail guides that taper from the ventral side areas towards the dorsal side areas and the upper and lower ends on the insert being arranged complementary to the dovetail guides, the insert being coupled to one of the upper and lower sections by a screw;

wherein an end of the second axle is spaced from an end of the third axle by a gap.

2. The intervertebral implant according to claim 1, wherein the upper and the lower sections each comprise at least two drill holes running through from the ventral side areas to the apposition surfaces with longitudinal axes for receiving bone fixation devices.

3. The intervertebral implant according to claim 2, wherein the longitudinal axes of the drill holes make an angle γ with the central axis.

4. The intervertebral implant according to claim 3, wherein the angle γ lies in a range between 20 degrees and 65 degrees.

5. The intervertebral implant according to claim 2, wherein the longitudinal axes of the drill holes as seen from the ventral side areas diverge from the inner surfaces against the apposition surfaces.

6. The intervertebral implant according to claim 2, wherein the drill holes are conically tapered towards the apposition surfaces.

7. The intervertebral implant according to claim 2, wherein the drill holes have an internal thread.

* * * * *